US012758127B2

(12) United States Patent
Chen

(10) Patent No.: US 12,758,127 B2
(45) Date of Patent: Oct. 13, 2026

(54) BIO-SENSING DEVICE

(71) Applicant: Taiwan-Asia Semiconductor Corporation, Hsinchu City (TW)

(72) Inventor: Chun-Ko Chen, Hsinchu City (TW)

(73) Assignee: TAIWAN-ASIA SEMICONDUCTOR CORPORATION, Hsinchu City (TW)

( * ) Notice: Subject to any disclaimer, the term of this patent is extended or adjusted under 35 U.S.C. 154(b) by 240 days.

(21) Appl. No.: 18/797,014

(22) Filed: Aug. 7, 2024

(65) Prior Publication Data

US 2025/0194965 A1 Jun. 19, 2025

(30) Foreign Application Priority Data

Dec. 15, 2023 (TW) ................................ 112149124

(51) Int. Cl.

| | |
|---|---|
| ***A61B 5/1455*** | (2006.01) |
| ***H10F 55/255*** | (2025.01) |
| ***H10F 77/30*** | (2025.01) |
| ***H10F 77/50*** | (2025.01) |

(52) U.S. Cl.

CPC ......... *A61B 5/1455* (2013.01); *H10F 55/255* (2025.01); *H10F 77/337* (2025.01); *H10F 77/50* (2025.01)

(58) Field of Classification Search

None

See application file for complete search history.

(56) References Cited

U.S. PATENT DOCUMENTS

| | | | | |
|---|---|---|---|---|
| 2018/0360352 | A1* | 12/2018 | Ohno | A61B 5/1455 |
| 2019/0090806 | A1* | 3/2019 | Clavelle | A61B 5/02427 |
| 2019/0246922 | A1* | 8/2019 | Matsuo | A61B 5/02438 |
| 2020/0168757 | A1* | 5/2020 | Lin | A61B 5/02141 |
| 2021/0153810 | A1* | 5/2021 | Min | G01N 21/35 |
| 2022/0045247 | A1* | 2/2022 | Wang | H10F 55/255 |
| 2023/0363669 | A1* | 11/2023 | Lee | A61B 5/0075 |
| 2025/0331815 | A1* | 10/2025 | Bai | A61B 8/5223 |

FOREIGN PATENT DOCUMENTS

| | | | |
|---|---|---|---|
| CN | 216946834 | U | 7/2022 |
| CN | 115586615 | A | 1/2023 |
| TW | 201928409 | A | 7/2019 |

* cited by examiner

*Primary Examiner* — Ryan Crockett

(74) *Attorney, Agent, or Firm* — MUNCY, GEISSLER, OLDS & LOWE, P.C.

(57) ABSTRACT

A bio-sensing device is provided, which includes a carrier substrate, a light source disposed on the carrier substrate, a photodiode sensor disposed on the carrier substrate and laterally spaced apart from the light source, a light-blocking wall disposed on the carrier substrate and located between the light source and the photodiode sensor, a cover glass, a dual-band filter coated on a front surface of the cover glass, a first optical adhesive formed on a back surface of the cover glass, and a second optical adhesive covering the carrier substrate, the light source, the photodiode sensor and the light-blocking wall, and being used to be bonded with the first optical adhesive. The first optical adhesive has been cured when the second optical adhesive is bonded with the first optical adhesive, and the second optical adhesive is cured by irradiation with ultraviolet light after being in contact with the first optical adhesive.

11 Claims, 5 Drawing Sheets

1

BIO-SENSING DEVICE

CROSS-REFERENCES TO RELATED APPLICATIONS

This application claims priority to Taiwan Patent Application No. 112149124 filed on Dec. 15, 2023, which is hereby incorporated by reference in its entirety.

BACKGROUND OF THE INVENTION

Field of the Invention

The present invention relates to a bio-sensing device, particularly an optical bio-sensing device.

Description of the Related Art

In recent years, non-invasive bio-sensing devices (especially optical bio-sensing devices) have been widely used in people's daily lives for purposes such as activity tracking, health management, and disease detection. These devices provide users with various physiological information, such as heart rate, blood oxygen saturation, blood pressure, and blood glucose, etc.

Bio-sensing devices (e.g., blood glucose sensing devices) usually include a cover glass (CG) with a filter coating layer on top. The filter coating layer may be formed by vacuum coating on the front surface of the cover glass. However, due to stress-induced warpage caused by coating, thinner glass thickness or larger glass size results in greater warpage. This phenomenon poses challenges when subsequently bonding the large cover glass to the light emitting/receiving module (which includes a light source and a light sensor) and thus, may require additional compensation and adjustments to the overall optical characteristics of the device.

To address the issue of excessive warpage, it has been proposed to coat optical films on both sides. This involves correspondingly coating the back surface of the cover glass with an optical coating layer of the same thickness and the same stress-induced warpage. However, this approach requires two vacuum processes, which greatly increases the manufacturing cost of the optical sensing device, and thus, facing the problem of high manufacturing cost.

In light of this, finding solutions to the stress-induced warpage issue caused by the coating on the cover glass of bio-sensing devices without significantly increasing the manufacturing cost is still an ongoing goal in the industry.

SUMMARY OF THE INVENTION

An objective of the present invention is to provide a technical solution to the problem of stress-induced warpage of the cover glass of a bio-sensing device caused by coating. The present invention solves the problem of stress-induced warpage by coating a dual-band filter on the front surface of the cover glass and forming an optical adhesive having a desired thickness on the back surface of the cover glass, for example, by using a dispensing method to apply the optical adhesive and then curing it once or more times for thereby achieving the same stress levels and directions on both sides of the cover glass.

Unlike the coating layers in the prior art, which are infrared light bandpass films that do not allow ultraviolet (UV) light to pass through, the present invention designs and utilizes a dual-band filter that allows UV and infrared light to pass through while blocking the visible light spectrum. This allows the subsequent process to bond the large cover glass to the light emitting/receiving module (which includes a light source and a light sensor) using a UV-curable adhesive and to cure the UV-curable adhesive with a UV curing process. Accordingly, since the formation and curing of the optical adhesive involves a non-vacuum process, and the dual-band filter on the front surface of the cover glass also has the property of UV light transmittance, the present invention can effectively solve the stress-induced warpage issue of the cover glass caused by coating in a cost-effective and faster process.

To achieve the above objective, the present invention discloses a bio-sensing device, including a carrier substrate, a light source disposed on the carrier substrate, a photodiode sensor disposed on the carrier substrate and laterally spaced apart from the light source, a light-blocking wall disposed on the carrier substrate and located between the light source and the photodiode sensor, a cover glass, a dual-band filter coated on a front surface of the cover glass, a first optical adhesive formed on a back surface of the cover glass, and a second optical adhesive covering the carrier substrate, the light source, the photodiode sensor and the light-blocking wall, and being used to be bonded with the first optical adhesive. The first optical adhesive has been cured when the second optical adhesive is bonded with the first optical adhesive, and the second optical adhesive is cured by irradiation with ultraviolet light after being in contact with the first optical adhesive.

In an example, the dual-band filter has a light transmittance greater than 60% for ultraviolet light, a light transmittance greater than 90% for infrared light, and a light transmittance less than 5% for visible light.

In an example, the dual-band filter is formed a first material layer and a second material layer alternately stacked to create a multilayer structure, and the first material layer is made of one of tantalum pentoxide ($Ta_2O_5$) and titanium dioxide ($TiO_2$), and the second material layer is made of silicon dioxide ($SiO_2$).

In an example, the multilayer structure of the dual-band filter has 40 to 60 layers, and a thickness of the dual-band filter is between 3 um and 6 um.

In an example, the first optical adhesive is one of a thermosetting adhesive or a UV-curable adhesive.

In an example, a thickness of the first optical adhesive is between 1 um and 20 um and has a light transmittance greater than 90%.

In an example, the thickness of the first optical adhesive is stress-matched with a thickness of the dual-band filter with respect to the cover glass.

In an example, the first optical adhesive is formed through a single coating process or multiple coating processes.

In an example, the second optical adhesive is a UV-curable adhesive and is formed through a single coating process.

In an example, the light source includes a light-emitting diode.

In an example, the light source includes a plurality of light-emitting diodes, and an additional light-blocking wall is provided between each two of the light-emitting diodes.

After referring to the drawings and the detailed description of embodiments described later, those of ordinary skill in the art can understand other objectives of the present invention, as well as the technical means and implementations of the present invention.

DETAILED DESCRIPTION OF THE PREFERRED EMBODIMENT

In the following description, the present invention will be explained with reference to various embodiments thereof. These embodiments of the present invention are not intended to limit the present invention to any specific environment, application or particular method for implementations described in these embodiments. Therefore, the description of these embodiments is for illustrative purposes only and is not intended to limit the present invention. It shall be appreciated that, in the following embodiments and the attached drawings, partial elements not directly related to the present invention are omitted from the illustration, and dimensional proportions among individual elements and the numbers of each element in the accompanying drawings are provided only for ease of understanding but are not intended to limit the actual scale.

Figure 1:
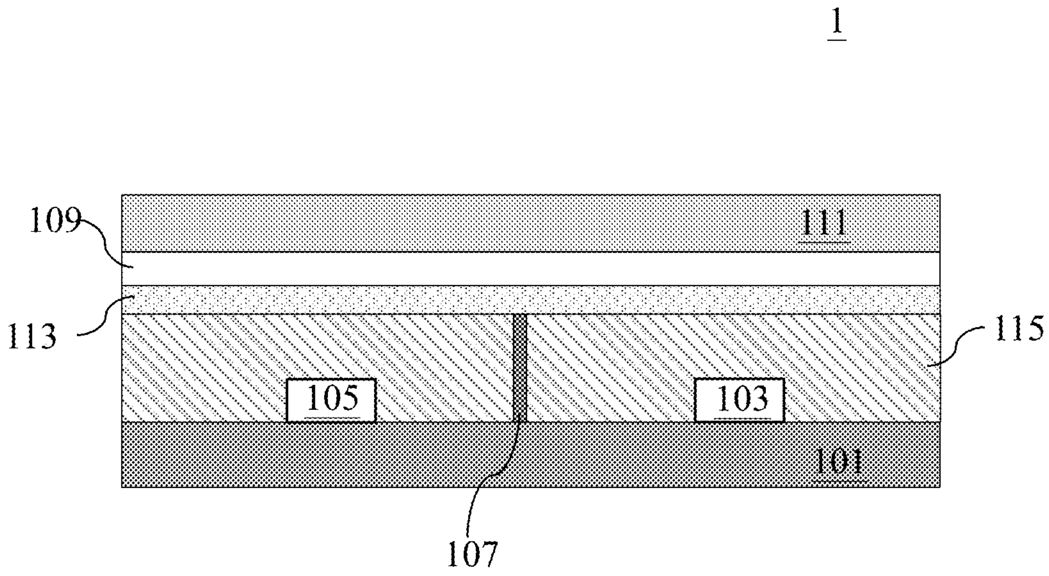
FIG. 1 is a schematic view of a bio-sensing device according to an embodiment of the present invention.

A bio-sensing device 1 according to an embodiment of the present invention is shown in FIG. 1. The bio-sensing device 1 includes a carrier substrate 101, a light source 103, a photodiode sensor 105, a light-blocking wall 107, a cover glass 109, a dual-band filter 111, a first optical adhesive 113 and a second optical adhesive 115.

The carrier substrate 101 may be a ceramic circuit board or a printed circuit board, but is not limited thereto. The light source 103 is disposed on the carrier substrate 101 and is electrically coupled to the carrier substrate 101. The light source 103 can be a light-emitting diode, e.g., a light-emitting diode generating infrared light. The wavelength of the infrared light generated by the light source 103 may be 900 nm to 17000 nm. In other embodiments, the light source 103 may be other light-emitting devices that can generate infrared light in a specific wavelength range. In other words, depending on different applications, the wavelength of the light generated by the light source 103 may vary. In addition, in other embodiments, the light source 103 may include a plurality of light-emitting diodes.

The photodiode sensor 105 is also disposed on the carrier substrate 101 and is electrically coupled to the carrier substrate 101. The photodiode sensor 105 and the light source 103 are laterally spaced apart from each other. The photodiode sensor 105 may be an indium gallium arsenide (InGaAs) photodiode sensor, but is not limited thereto. The wavelength range of light that the photodiode sensor 105 can detect is between 900 nm to 1700 nm, but is not limited thereto, and may vary depending on different applications.

The light-blocking wall 107 is disposed on the carrier substrate 101 and is located between the light source 103 and the photodiode sensor 105. The light-blocking wall 107 can ensure that the light emitted by the light source 103 is not directly received by the photodiode sensor 105. For example, the light-blocking wall 107 may be made of epoxy resin (Epoxy), which has a matte black appearance after curing so that neither visible light nor invisible light can penetrate.

The dual-band filter 111 is coated on a front surface of the cover glass 109. The dual-band filter 111 has a light transmittance greater than 60% for ultraviolet light (e.g., the light with a wavelength between 350 nm and 380 nm) and has a light transmittance greater than 90% for infrared light (e.g., the light with a wavelength between 900 nm and 1700 nm). In addition, the dual-band filter 111 has a light transmittance less than 5% for visible light (e.g., light with a wavelength between 400 nm and 800 nm).

In other words, the dual-band filter 111 has a dual-channel transmission design for UV and infrared light. The transmittance of the dual-band filter 111 for the UV light region must be greater than 60% to facilitate the subsequent curing of the second optical adhesive 115. The dual-band filter 111 must filter ambient light noise so that the transmittance for the visible light region must be less than 5%. In addition, the transmittance of the dual-band filter 111 for the infrared light region must be greater than 90% to allow the light generated by the light source 103 to pass through.

The dual-band filter 111 is made of first and second material layers alternately stacked to form a multilayer structure. For example, the first material layer may be made of one of tantalum pentoxide ($Ta_2O_5$) and titanium dioxide ($TiO_2$), and the second material layer may be made of silicon dioxide ($SiO_2$). The multilayer structure of the dual-band filter 111 may have 40 to 60 layers, and a thicknesses of the dual-band filter 111 may be between 3 um and 6 um.

The first optical adhesive 113 is formed on the back surface of the cover glass 109. The first optical adhesive 113 with a desired thickness may be formed by using a dispensing method to apply an optical adhesive on the back surface of the cover glass 109 and cure it once or more times (that is, performing curing after each coating application). Accordingly, through the formation of the first optical adhesive 113, the present invention can realize a design with the same stress levels and directions on both sides of the cover glass 109 for thereby solving the problem of stress-induced warpage.

For example, the first optical adhesive 113 may be a thermosetting adhesive or a UV-curable adhesive. The thickness of the first optical adhesive may range from 1 um to 20 um and has a light transmittance greater than 90%. Therefore, by stress matching the thickness of the first optical adhesive 113 and the thickness of the dual-band filter 111 with respect to the cover glass 109, the present invention can effectively solve the problem of stress-induced warpage.

The second optical adhesive 115 covers the carrier substrate 101, the light source 103, the photodiode sensor 105 and the light-blocking wall 107. The second optical adhesive 115 is used to bond with the first optical adhesive 113. The second optical adhesive may be a UV-curable adhesive and is formed through a single coating process. As mentioned above, the first optical adhesive 113 is cured after each coating application. Therefore, the first optical adhesive 113 has been cured when the second optical adhesive 115 is bonded with the first optical adhesive 113, and the second optical adhesive 115 is cured by irradiation with ultraviolet light after being in contact with the first optical adhesive 113.

Figure 2A:
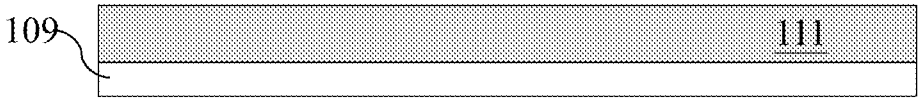
FIGS. 2A-2E are schematic views depicting the process steps for manufacturing the bio-sensing device shown in FIG. 1.
Figure 2B:
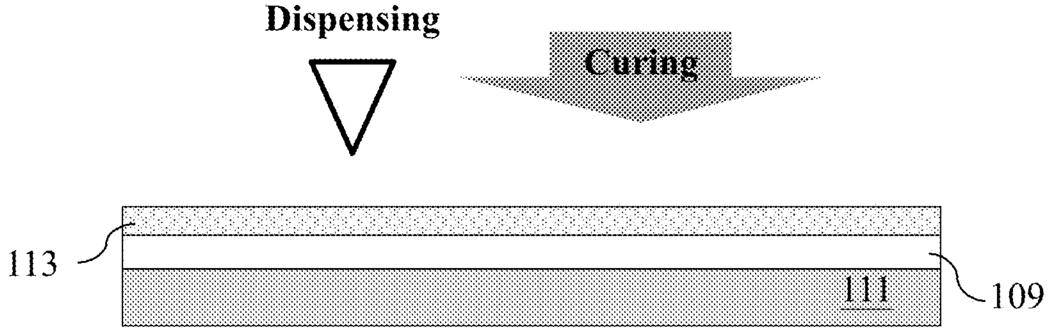

FIGS. 2A-2E are schematic views depicting the process steps for manufacturing the bio-sensing device shown in FIG. 1. First, as shown in FIG. 2A, the dual-band filter 111 is coated (e.g., by vapor deposition) on the front surface of the cover glass 109. Next, as shown in FIG. 2B, the first optical adhesive 113 with a desired thickness is formed by using a dispensing method to apply an optical adhesive on the back surface of the cover glass 109 and cure it once or more times.

Figure 2C:
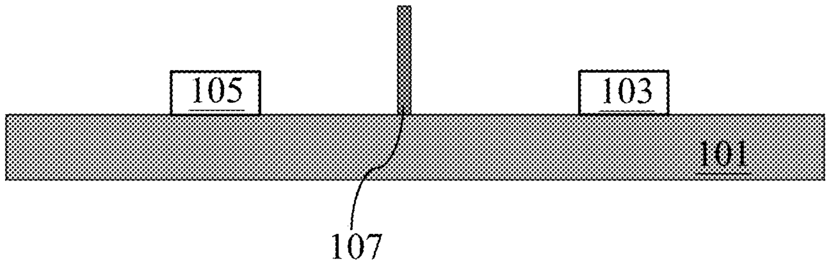
Figure 2D:
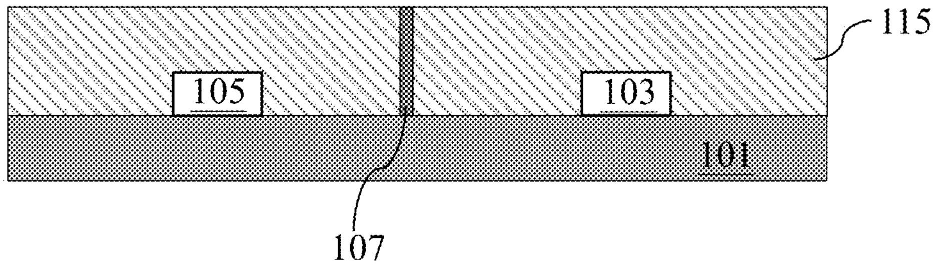
Figure 2E:
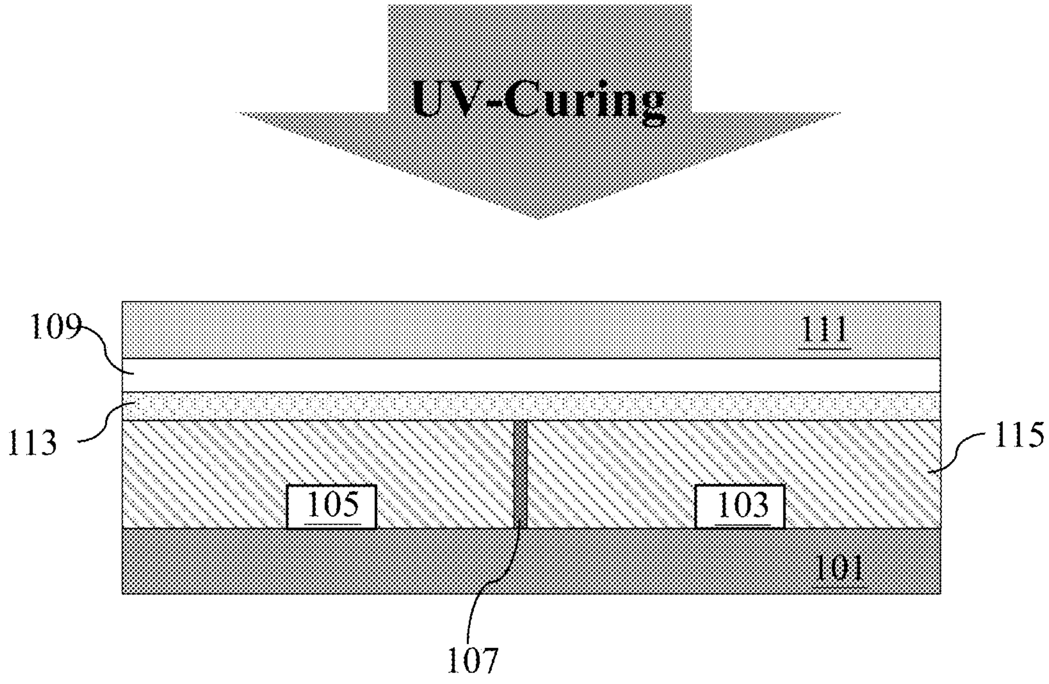

In addition, as shown in FIG. 2C, a carrier substrate 101 is provided, and a light source 103, a photodiode sensor 105 and a light-blocking wall 107 are provided thereon. After the structures of FIG. 2B and FIG. 2C are constructed, the carrier substrate 101, the light source 103, the photodiode sensor 105 and the light-blocking wall 107 are covered by the second optical adhesive 115, as shown in FIG. 2D. Finally, the structure of FIG. 2B is bonded to the structure of FIG. 2D so that the first optical adhesive 113 and the second optical adhesive 115 are in contact and irradiated with the UV light. Accordingly, the UV light passes through the dual-band filter 111, the cover glass 109 and the first optical adhesive 113 and irradiates the second optical adhesive 115 to cure the second optical adhesive 115.

It should be noted that there is no sequence between the production of the structure in FIG. 2B and the production of the structure in FIG. 2D. In other words, it does not matter whether the two structures are produced at the same time or one after another, and both are possible production sequences.

Figure 3:
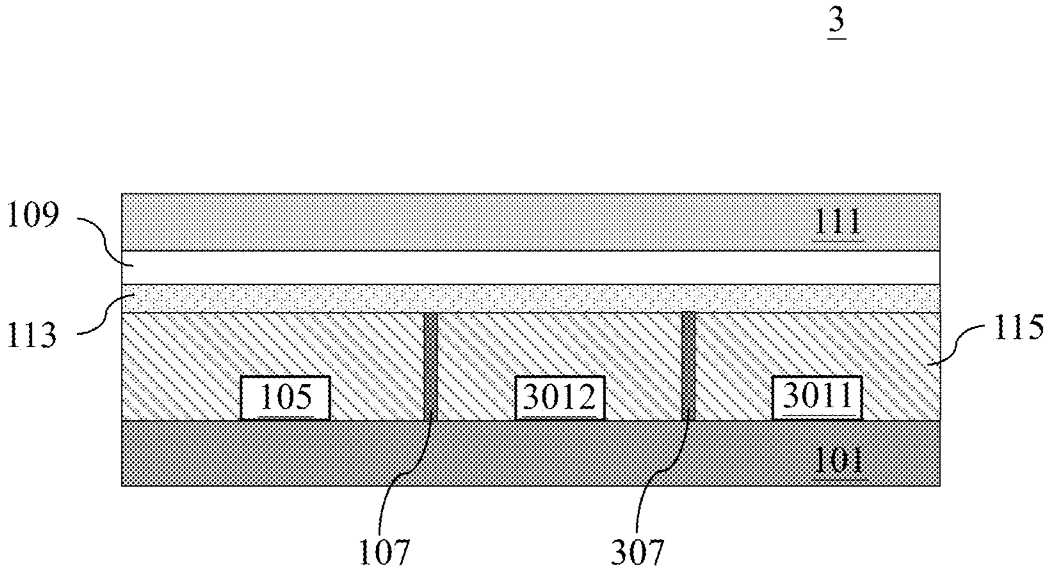
FIG. 3 is a schematic view of a bio-sensing device according to an embodiment of the present invention.

FIG. 3 is a schematic view of a bio-sensing device 3 according to an embodiment of the present invention. Different from the bio-sensing device 1 shown in FIG. 1, the light source of the bio-sensing device 3 includes a plurality of light-emitting diodes, and an additional light-blocking wall is provided between each two of the light-emitting diodes. Here, two light-emitting diodes 3011 and 3012 are used as an example. As shown in FIG. 3, an additional light-blocking wall 307 between the light-emitting diodes 3011 and 3012 is provided for adjusting or improving light characteristics. However, those skilled in the art will understand that in other embodiments, depending on design requirements, the bio-sensing device may include more than two light-emitting diodes and thus, no further description is given here.

In summary, the present invention can effectively solve the problem of stress-induced warpage by coating a dual-band filter on the front surface of the cover glass to allow the UV and infrared light to pass through and to block the visible light spectrum, and by applying an optical adhesive and then curing it once or more times to form the optical adhesive with a desired thickness on the back surface of the cover glass for thereby achieving the same stress levels and directions on both sides of the cover glass. Furthermore, in the present invention, the UV-curable adhesive is used to bond the large cover glass to the light emitting/receiving module (which includes a light source and a light sensor), and the UV-curable adhesive is cured after bonding based on the property that the UV light can pass through the dual-band filter. Accordingly, the present invention can effectively solve the stress-induced warpage issue of the cover glass caused by coating in a cost-effective and faster process, making it more suitable for any portable device (such as handheld devices or wearable devices).

The above embodiments are used only to illustrate the implementations of the present invention and to explain the technical features of the present invention, and are not intended to limit the scope of the present invention. Any modifications or equivalent arrangements that can be easily accomplished by those skilled in this art are considered to fall within the scope of the present invention, and the scope of the present invention should be limited by the claims of the patent application.

What is claimed is:

1. A bio-sensing device, comprising:
a carrier substrate;
a light source disposed on the carrier substrate;
a photodiode sensor disposed on the carrier substrate and laterally spaced apart from the light source;
a light-blocking wall disposed on the carrier substrate and located between the light source and the photodiode sensor;
a cover glass;
a dual-band filter coated on a front surface of the cover glass;
a first optical adhesive formed on a back surface of the cover glass; and
a second optical adhesive covering the carrier substrate, the light source, the photodiode sensor and the light-blocking wall, and being used to be bonded with the first optical adhesive;
wherein the first optical adhesive has been cured when the second optical adhesive is bonded with the first optical adhesive, and the second optical adhesive is cured by irradiation with ultraviolet light after being in contact with the first optical adhesive.

2. The bio-sensing device of claim 1, wherein the dual-band filter has a light transmittance greater than 60% for ultraviolet light, a light transmittance greater than 90% for infrared light, and a light transmittance less than 5% for visible light.

3. The bio-sensing device of claim 1, wherein the dual-band filter is formed by a first material layer and a second material layer alternately stacked to create a multilayer structure, and the first material layer is made of one of tantalum pentoxide ($Ta_2O_5$) and titanium dioxide ($TiO_2$), and the second material layer is made of silicon dioxide ($SiO_2$).

4. The bio-sensing device of claim 3, wherein the multilayer structure of the dual-band filter has 40 to 60 layers, and a thickness of the dual-band filter is between 3 um and 6 um.

5. The bio-sensing device of claim 1, wherein the first optical adhesive is one of a thermosetting adhesive or a UV-curable adhesive.

6. The bio-sensing device of claim 1, wherein a thickness of the first optical adhesive is between 1 um and 20 um and has a light transmittance greater than 90%.

7. The bio-sensing device of claim 6, wherein the thickness of the first optical adhesive is stress-matched with a thickness of the dual-band filter with respect to the cover glass.

8. The bio-sensing device of claim 6, wherein the first optical adhesive is formed through a single coating process or multiple coating processes.

9. The bio-sensing device of claim 1, wherein the second optical adhesive is a UV-curable adhesive and is formed through a single coating process.

10. The bio-sensing device of claim 1, wherein the light source comprises a light-emitting diode.

11. The bio-sensing device of claim 1, wherein the light source comprises a plurality of light-emitting diodes, and an additional light-blocking wall is provided between each two of the light-emitting diodes.

* * * * *